(12) United States Patent
Hwang

(10) Patent No.: US 7,578,805 B2
(45) Date of Patent: Aug. 25, 2009

(54) BLOOD COLLECTION DEVICE

(75) Inventor: Charles G. Hwang, Ridgewood, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 10/437,510

(22) Filed: May 14, 2003

(65) Prior Publication Data
US 2003/0216687 A1 Nov. 20, 2003

Related U.S. Application Data

(60) Provisional application No. 60/380,592, filed on May 15, 2002.

(51) Int. Cl.
*A61M 5/32* (2006.01)
(52) U.S. Cl. .................................................... 604/192
(58) Field of Classification Search ............... 604/110, 604/263, 165.03, 177, 93.01, 117, 158, 162, 604/163, 164.01, 164.04, 164.07, 164.08, 604/165.01, 165.02, 165.04, 174, 187, 192, 604/197, 198, 264, 272; 128/919; 600/121–125; 83/397, 478, 544; 74/613; 433/116; 112/235, 112/237, 240
See application file for complete search history.

(56) References Cited

U.S. PATENT DOCUMENTS

| | | | | |
|---|---|---|---|---|
| 4,170,993 A | * | 10/1979 | Alvarez | 604/180 |
| 4,850,961 A | * | 7/1989 | Wanderer et al. | 604/508 |
| 4,892,521 A | | 1/1990 | Laico et al. | |
| 4,898,589 A | * | 2/1990 | Dolgin et al. | 604/198 |
| 4,911,706 A | * | 3/1990 | Levitt | 604/198 |
| 4,941,881 A | | 7/1990 | Masters et al. | |
| 5,026,356 A | | 6/1991 | Smith | |
| 5,030,212 A | | 7/1991 | Rose | |
| 5,051,109 A | | 9/1991 | Simon | |
| 5,059,184 A | | 10/1991 | Dyke | |
| 5,112,311 A | | 5/1992 | Utterberg et al. | |
| 5,120,320 A | | 6/1992 | Fayngold | |
| 5,152,751 A | | 10/1992 | Kozlowski | |
| 5,192,275 A | | 3/1993 | Burns | |
| 5,266,072 A | | 11/1993 | Utterberg et al. | |
| 5,290,264 A | | 3/1994 | Utterberg | |
| 5,312,372 A | | 5/1994 | DeHarde et al. | |

(Continued)

FOREIGN PATENT DOCUMENTS

JP 8-206195 8/1996

(Continued)

*Primary Examiner*—Kevin C Sirmons
*Assistant Examiner*—Elizabeth R Moulton
(74) *Attorney, Agent, or Firm*—Mark J. Schildkraut; The Webb Law Firm

(57) ABSTRACT

The present invention is directed to a shieldable needle device. The shieldable needle device includes a housing, a needle cannula, a tip guard and an elongated flexibly resilient drive mechanism. The housing includes a longitudinal slot that extends along a wall of the housing. The drive mechanism is bent within the housing and includes a first end which extends through the longitudinal slot and a second end which is anchored to the tip guard. Upon movement of the first end along the longitudinal slot, the second end extends and moves the tip guard from a retracted position to an extended position thereby protectively surrounding a tip of the needle cannula.

21 Claims, 8 Drawing Sheets

U.S. PATENT DOCUMENTS

| | | |
|---|---|---|
| 5,334,158 A | 8/1994 | McLees |
| 5,423,766 A | 6/1995 | DiCesare |
| 5,425,720 A | 6/1995 | Rogalsky et al. |
| 5,462,533 A * | 10/1995 | Daugherty ............. 604/164.01 |
| 5,549,570 A | 8/1996 | Rogalsky |
| 5,569,202 A | 10/1996 | Kovalic et al. |
| 5,584,818 A * | 12/1996 | Morrison .................... 604/192 |
| 5,676,658 A | 10/1997 | Erskine |
| 5,746,718 A | 5/1998 | Steyn |
| 5,810,784 A | 9/1998 | Tamaro |
| 5,853,393 A | 12/1998 | Bogert |
| 5,879,331 A | 3/1999 | Osterlind |
| 5,910,132 A | 6/1999 | Schultz |
| 5,919,168 A | 7/1999 | Wheeler |
| 5,925,020 A | 7/1999 | Nestell |
| 6,050,976 A * | 4/2000 | Thorne et al. .......... 604/164.01 |
| 6,186,979 B1 | 2/2001 | Dysarz |
| RE37,110 E | 3/2001 | Hollister |
| 6,228,066 B1 | 5/2001 | Zhadanov et al. |
| 6,287,278 B1 | 9/2001 | Woehr et al. |
| 2001/0031949 A1 * | 10/2001 | Asbaghi ..................... 604/198 |

FOREIGN PATENT DOCUMENTS

| | | |
|---|---|---|
| WO | WO93/01851 | 2/1993 |

* cited by examiner

BLOOD COLLECTION DEVICE

CROSS REFERENCE TO RELATED APPLICATIONS

This application claims the benefit of U.S. Provisional Patent Application Ser. No. 60/380,592 filed on May 15, 2002 which is incorporated by reference in its entirety.

BACKGROUND OF THE INVENTION

1. Field of the Invention

The present invention relates to safety needle devices for safe and convenient handling of needles. More particularly, the present invention relates to a shieldable needle device having a forward moving safety shield for protection from a used needle tip.

2. Description of Related Art

Disposable medical devices having medical needles are used for administering medication or withdrawing fluid from the body of a patient. Such disposable medical devices typically include blood-collecting needles, fluid handling needles and assemblies thereof. Current medical practice requires that fluid containers and needle assemblies used in such devices be inexpensive and readily disposable. Consequently, existing blood collection devices typically employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a blood collection tube or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies commonly employ a safety shield that can be moved into shielding engagement with a used needle cannula to minimize risk of an accidental needle stick.

For example, U.S. Pat. No. 4,892,521 to Laico et al., discloses a telescoping protective cover, which utilizes a pair of guide members to extend a telescoping tip guard to a shielding position. The guide members are diametrically located and function to guide the tip guard to the protective position, and may be spring biased.

U.S. Pat. No. 5,423,766 to DiCesare discloses a safety shield including a tip guard that is slideably movable along the needle from a proximal position to a distal position. The safety shield utilizes a spring tether which is connected to a guard and an anchor. The tether is deflected into a loop, with the guard and anchor preventing the tether from springing open.

Such prior art devices are typically difficult to manufacture, and require complex operation to operate. In view of the foregoing, a need exists for a blood collection set including a shieldable needle device that achieves secure and effective shielding of a used needle cannula, which is easy to manufacture and is simple and safe to operate.

SUMMARY OF THE INVENTION

The present invention is directed to a shieldable needle device. The shieldable needle device includes a housing with a forward end, a rearward end, an internal opening extending therethrough, and a longitudinal slot which extends along a wall of the housing between the forward and rearward end and through the wall into the internal opening. The shieldable needle device further includes a needle cannula having a forward end and a rearward end with the needle cannula extending from the forward end of the housing, and a tip guard which is axially movable along the needle cannula between a retracted position, in which the forward end of the needle cannula is exposed, and an extended position, in which the tip guard protectively surrounds the forward end of the needle cannula. The shieldable needle device also includes an elongated flexibly resilient drive mechanism which is bent within the housing, with a first end extending through the longitudinal slot at a position adjacent the forward end of the housing and a second end anchored to the tip guard. Movement of the first end of the drive mechanism along the longitudinal slot causes the second end of the drive mechanism to extend, thereby moving the tip guard from the retracted position to an extended position, protectively surrounding the forward end of the needle cannula. Desirably, the drive mechanism is bent around a bend of about 180° between the first end and the second end.

In particularly desirable embodiments, the shieldable needle device includes generally planar wings for the housing, thereby forming a wingset. The drive mechanism is desirably in the form of the wire, and preferably includes a tab to activate the drive mechanism. For example, the tab may extend through the longitudinal slot of the housing, with a profile for accommodating a user's finger. Upon movement of the drive mechanism, desirably with the use of the tab, along the longitudinal slot in a direction toward the rearward end of the housing, the drive mechanism extends from the bent position to the extended position, thereby moving the tip guard to a forward position, protectively surrounding the forward end of the needle. In this manner, shielding of the needle tip can be accomplished by moving the tab in a direction away from the needle tip, providing an additional safety feature.

In a further embodiment, the present invention is directed to a shieldable blood collection set which includes a needle device as described above, connected to a fixture for a receptacle through a flexible tube. In particular, the needle device includes a housing, a needle cannula, and a tip guard axially movable along the needle cannula between a retracted position where a puncture tip of the needle cannula is exposed, and an extended position where the tip guard covers the puncture tip of the needle cannula. The needle device further includes an elongated flexibly resilient drive mechanism with a first end and a second end, having a bend of about 180° within the housing. The first end extends through a slot in the housing, and the second end is anchored to the tip guard.

Movement of the first end causes the second end to extend, thereby moving the tip guard from a retracted position to an extended position covering the puncture tip of the needle cannula.

DETAILED DESCRIPTION

Figure 1:
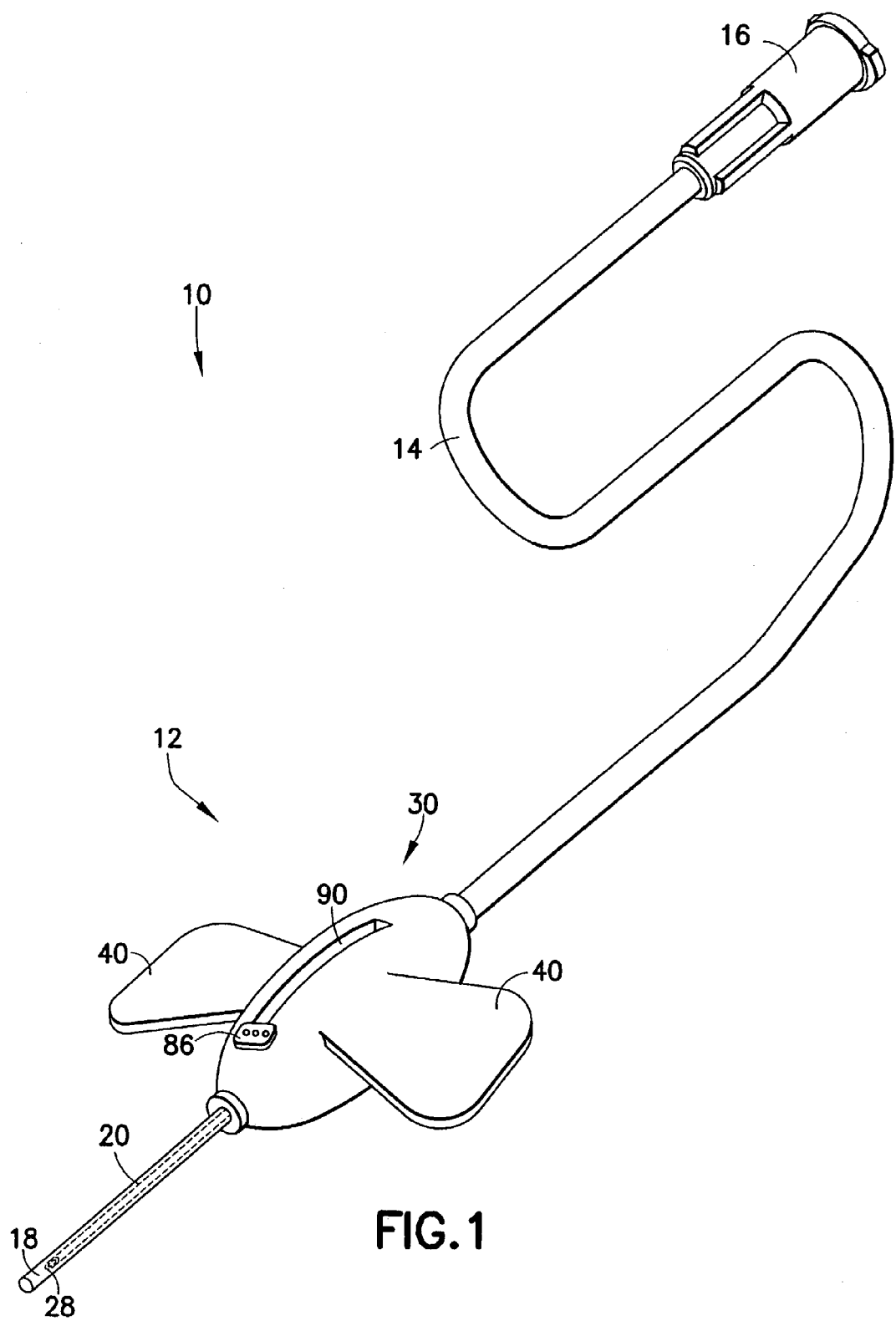
FIG. 1 is a perspective view of a blood collection set including a shieldable needle device, in accordance with the present invention.

Referring to the drawings in which like reference characters refer to like parts throughout the several views thereof, FIG. 1 illustrates a blood collection set, including a shieldable needle device in accordance with the present invention and the related features. The present invention is generally described in terms of a shieldable needle device. FIG. 1 illustrates the shieldable needle device in the form of a blood collection set 10, including a shieldable needle device 12. While described herein in terms of one embodiment of a blood collection set, the shieldable needle device of the present invention may be used with or incorporate other medical devices used in connection with a needle, such as a hypodermic syringe assembly, a hypodermic needle, a double-ended needle assembly for blood collection, an intravenous infusion set, or other handling devices or medical device assemblies that contain piercing elements.

As shown in FIG. 1, blood collection set 10 includes a shieldable needle device 12, a flexible tube 14 extending from needle device 12, a fixture 16 mounted to tube 14, and a packaging cover 18 removably mounted to portions of needle device 12 opposite tube 14, such as through frictional engagement. Shieldable needle device 12 of blood collection set 10 is shown in detail in FIGS. 2–5, and includes a needle cannula 20, a housing 30, a tip guard assembly 50 and an elongated flexibly resilient drive mechanism 80.

Needle cannula 20 includes a rearward end or proximal end 22 and a forward end or opposing distal end 24, with a lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture.

Needle device 12 further includes housing 30. Housing 30 is a unitary structure, desirably molded from a thermoplastic material. Housing 30 includes a rearward end or proximal end 32, an opposing forward end or distal end 34 and is defined by a rigid tubular wall 36 extending from rearward end 32 to forward end 34. Tubular wall 36 is characterized by an internal passageway 38 extending therethrough from proximal end 32 to distal end 34 of housing 30. The bottom surface of housing 30 may be generally planar or flat, which provides an effective surface to lie against the skin of a patient during use. Housing 30 may further include a pair of stabilizers 40 extending along tubular wall 36 at opposing sides thereof. Stabilizers 40 provide housing 30, and needle device 12, as a butterfly-type wingset assembly, assisting in positioning and placement of needle device and blood collection set 10 during blood collection procedures. Housing 30 further includes a longitudinal slot 90 extending along a top portion of tubular wall 36. Slot 90 extends longitudinally along wall 36 over a portion of wall 36 between proximal end 32 and distal end 34 of housing 30. Slot 90 includes a forward end stop 92 at a forward end of slot 90 adjacent distal end 34 of housing 30, and a rearward end stop 94 at a rearward end of slot 90 adjacent proximal end 32 of housing 30.

Figure 4:
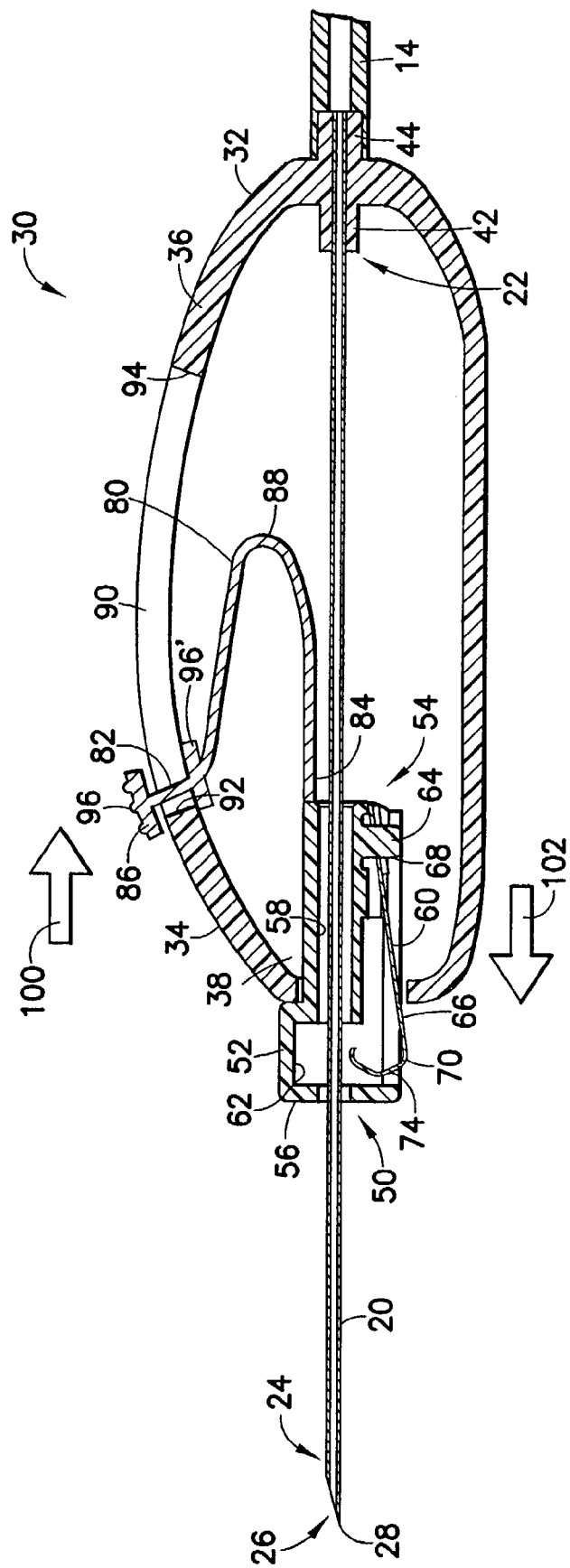
FIG. 4 is a cross-sectional view taken along line IV—IV of FIG. 2 of the housing with the needle device in a sampling state.
Figure 5:
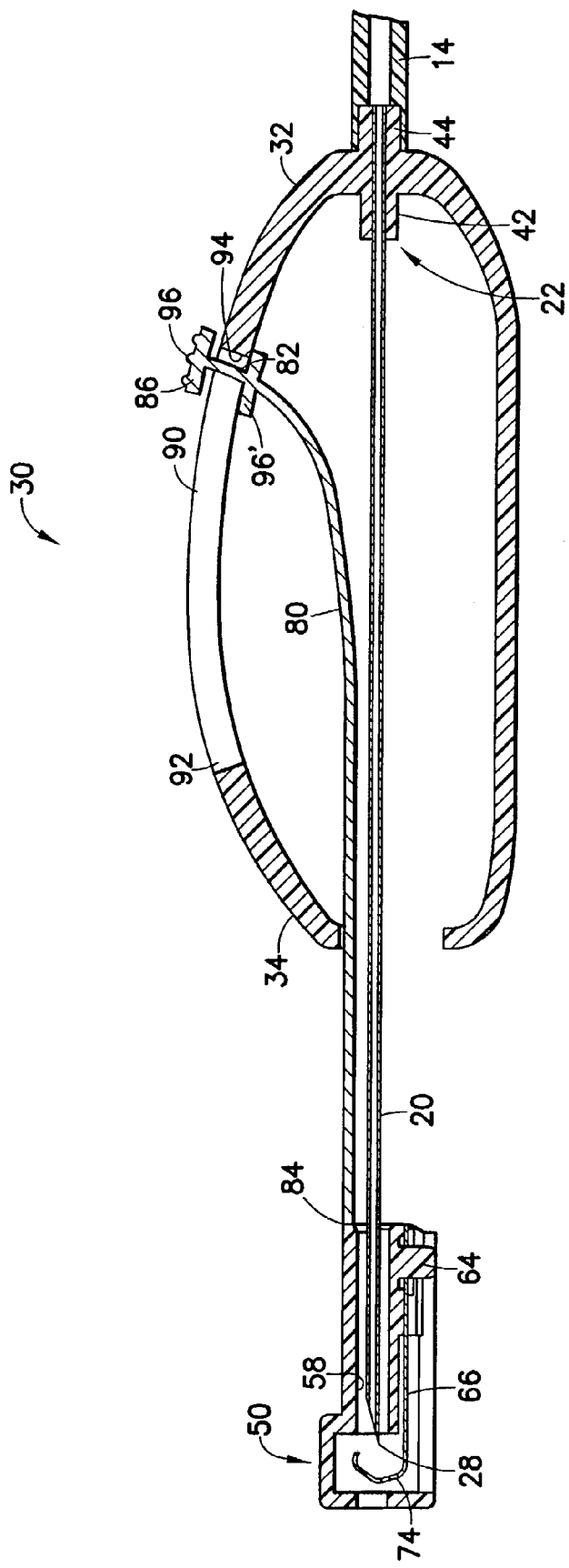
FIG. 5 is a cross-sectional view taken along line V—V of FIG. 3 of the housing with the needle device in a fully shielded state.

Needle cannula 20 is positioned within internal passageway 38 of housing 30, and extends from forward end 34 of housing 30. Desirably, needle cannula 20 and housing 30 are separate parts which are fixedly attached and secured through an appropriate medical grade adhesive or the like. For example, as shown in FIGS. 4 and 5, housing 30 may include a hub portion 42 extending from the rearward or proximal end 32 into or within internal passageway 38, with proximal end 22 of needle cannula 20 affixed to housing 30 at the hub portion 42. In such an embodiment, housing 30 may further include a nub 44 extending from the rearward or proximal end 32, for attachment with flexible tube 14. Alternatively, flexible tube 14 may extend within the internal passageway 38 of housing 30, with proximal end 22 of needle cannula 20 attached directly to flexible tube 14. In such an embodiment, proximal end 32 of housing 30 may be directly attached around flexible tube 14, such as by frictional engagement, or through an adhesive or the like.

Figure 3:
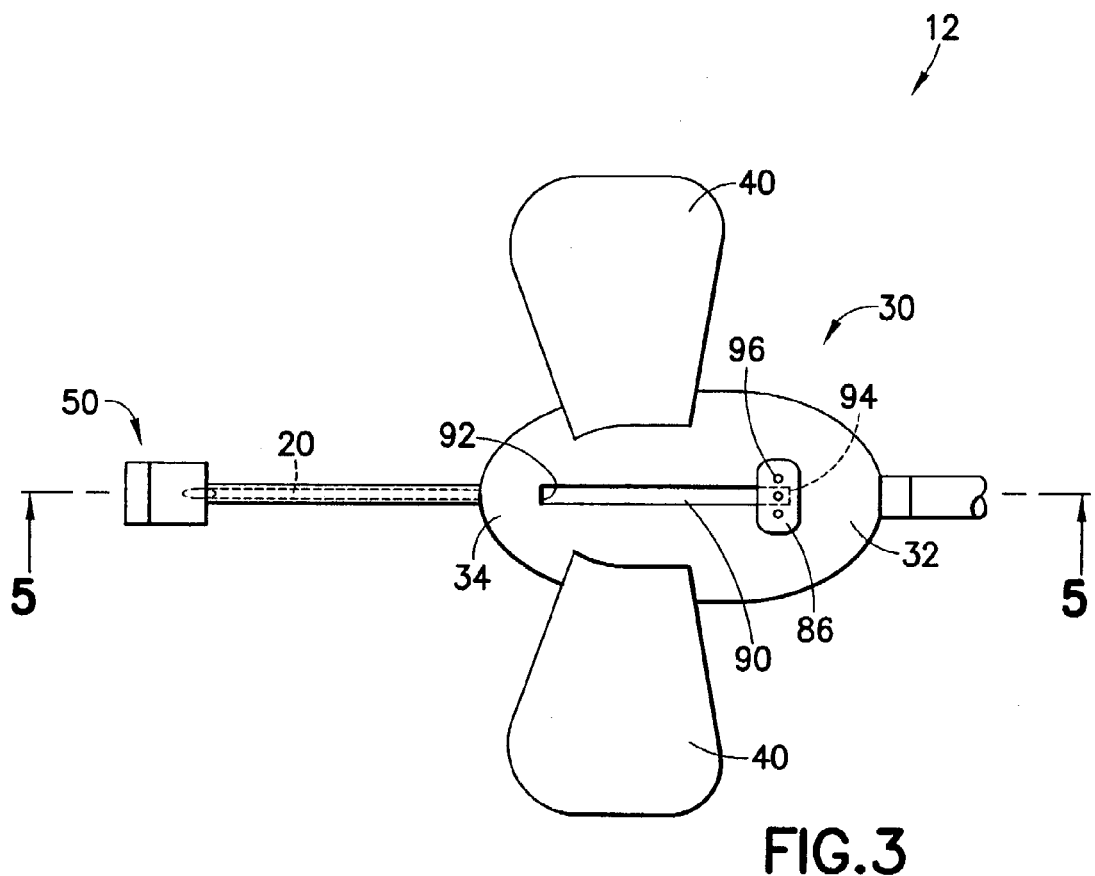
FIG. 3 is a top plan view of the needle device in FIG. 2 shown in a fully shielded state.
Figure 6:
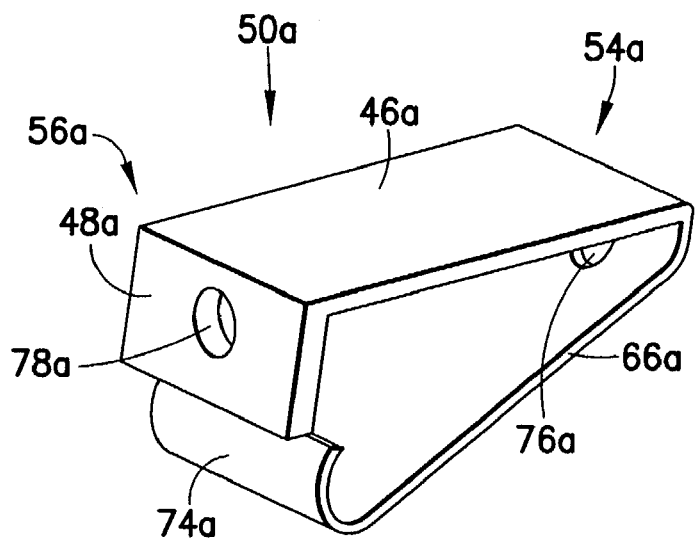
FIG. 6 is a perspective view of a tip guard in an alternate embodiment of the present invention.

Needle device 12 further includes tip guard assembly 50, which is movable along needle cannula 20 between a first rearward or retracted position adjacent housing 30, and a second forward or extended position adjacent puncture tip 28, as will be described in more detail herein. The tip guard assembly 50 may be any assembly capable of telescoping along needle cannula 20 to a position shielding the tip of the needle. For example, the tip guard assembly 50 may be of a two-piece construction as shown in FIGS. 3 and 4, or may be of a unitary, one-piece construction, as shown in FIG. 6. Tip guard assembly 50 as shown in FIGS. 4 and 5 includes a housing 52 and a protective clip 60. Housing 52 is a unitary structure, desirably molded from a thermoplastic material, including a rearward or proximal end 54, a forward or distal end 56, and an internal passage 58 extending between the ends. Portions of internal passage 58 adjacent distal end 56 define an enlarged clip receptacle 62. A clip mounting post 64 extends downwardly from housing 52 at a location near proximal end 54 of housing 52.

Clip 60 is unitarily stamped and formed from a resiliently deflectable metallic material. Clip 60 includes a planar spring leg 66 with a proximal end 68 and an opposed distal end 70. A mounting aperture (not shown) extends through spring leg 66 at a location near proximal end 68. The mounting aperture has a diameter approximately equal to or slightly less than the diameter of mounting post 64 of housing 52. As such, mounting post 64 can be forced through the mounting aperture when the axis of mounting post 64 and the axis of the mounting aperture are substantially co-linear. A lockout leg 74 extends angularly from distal end 70 of spring leg 66. Lockout leg 74 is bent back toward proximal end 68 of clip 60. The bends in lockout leg 74 enable secure protective engagement with puncture tip 28 of needle cannula 20 and further enable smooth axial sliding movement of tip guard assembly 50 along needle cannula 20.

In a retracted position, tip guard assembly 50 may be positioned along needle cannula 20 at any point adjacent housing 30. For example, as seen in FIG. 4, tip guard assembly 50 may be positioned within internal passageway 38 of housing 30 adjacent distal end 34, provided an opening is present through distal end 34 of housing 30 for tip guard assembly 50 to pass through during extension thereof. Alternatively, tip guard assembly 50 may be positioned outside of housing 30 at a position adjacent distal end 34 when in the retracted position.

Housing 30 and tip guard assembly 50 are interconnected through drive mechanism 80. Drive mechanism 80 provides for activation of the safety shielding feature of shieldable needle device 12 through axial movement of tip guard assembly 50 along needle cannula 20 from the retracted position adjacent housing 30 to an extended position adjacent puncture tip 28, as will be described in more detail herein.

Drive mechanism 80 is an elongated flexibly resilient structure. As employed herein, "flexibly resilient" refers to a structure which is generally stiff in a relaxed state, and which is able to bend easily and to easily resume its original shape after bending. Drive mechanism 80 may be constructed of any material capable of providing such properties, and is desirably constructed of a polymeric or metallic material. Moreover, drive mechanism 80 may include any profile, such as a round, wire-like profile, or ribbon-like profile. Preferably, drive mechanism 80 is an extent of wire. It is also contemplated that drive mechanism 80 may be a material which automatically resumes its original shape after being bent, in that it is in a biased state when bent.

Drive mechanism 80 includes a first end 82 and a second end 84, with second end 84 attached to tip guard assembly 50. First end 82 of drive mechanism 80 may further include a trigger or tab 86 which may be integrally formed therewith or separately attached thereto. Tab 86 desirably includes a surface having a profile for accommodating a user's finger, such as ribs or bumps 96. Tab 86 extends through longitudinal slot 90, and assists in actuating drive mechanism 80. Drive mechanism 80 further includes an extension 96' which extends from drive mechanism 80 within housing 30 and slides or glides against an interior surface thereof adjacent longitudinal slot 90, to maintain drive mechanism 80 within longitudinal slot 90 with tab 86 thereagainst.

Figure 2:
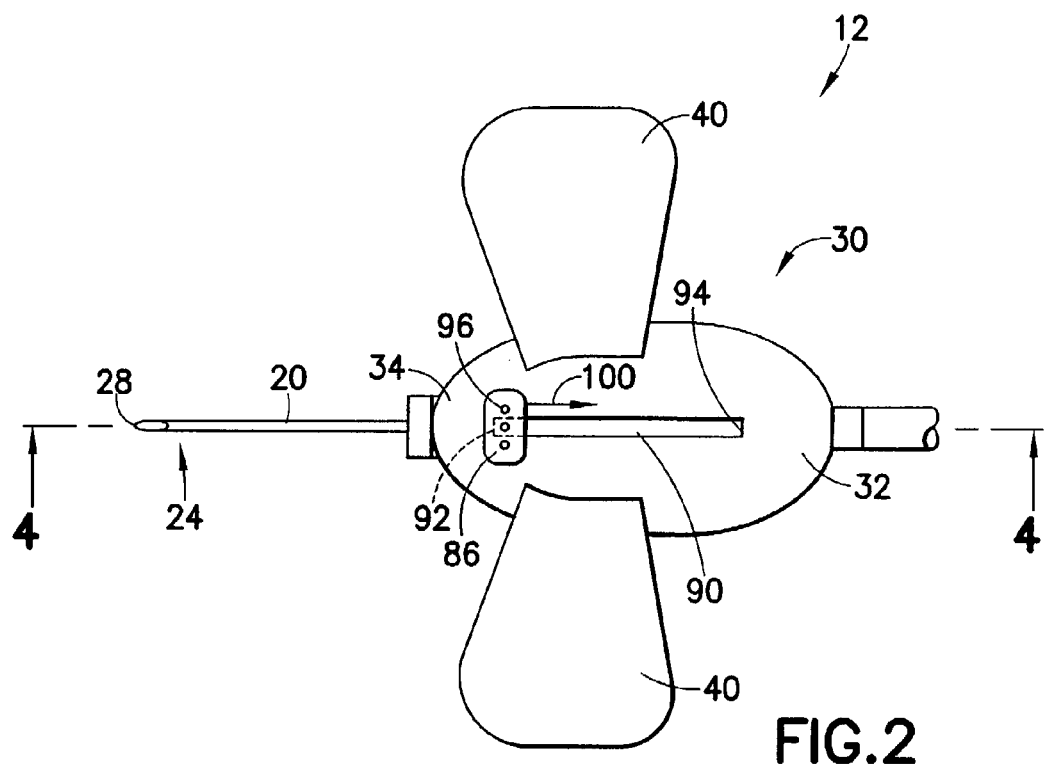
FIG. 2 is a top plan view of a needle device in accordance with the present invention shown in a retracted or sampling state.

As indicated, drive mechanism 80 provides for axial movement of tip guard assembly 50 between the retracted and extended position. Accordingly, when tip guard assembly 50 is in the retracted position with the puncture tip 28 of needle cannula 20 exposed, as shown in FIGS. 2 and 4, first end 82 of drive mechanism 80 including tab 86 extends through longitudinal slot 90 at forward end stop 92 located at a position adjacent distal end 34 of housing 30. Drive mechanism 80 extends toward the rearward or proximal end 32 of housing 30, and is bent around a bend 88 within internal passageway 38 of housing 30 between first end 82 of drive mechanism 80 and second end 84 of drive mechanism 80 as shown in FIG. 4. Bend 88 is preferably about 180°, with drive mechanism 80 further extending toward the distal end 34 of housing 30, toward the second end 84 of drive mechanism 80, which is attached to tip guard assembly 50.

External pressure exerted on tab 86 in a direction towards proximal end 32 of housing 30 or in a direction of arrow 100 along longitudinal slot 90, such as through a user's index finger, activates drive mechanism 80, thereby extending tip guard assembly 50 in a direction of arrow 102, from the retracted position to the extended position, to safely shield puncture tip 28.

More particularly, drive mechanism 80 is a stiff member which is bent into a biased state, as shown in FIG. 4. Movement of tab 86 towards the proximal end 32 of housing 30 along longitudinal slot 90 results in a biasing force exerted between first end 82 of drive mechanism 80 and second end 84 of drive mechanism 80 in opposing directions with respect to each other. Since first end 82 of drive mechanism 80 is attached to tab 86, first end 82 of drive mechanism 80 moves from forward end stop 92 to rearward end stop 94 along longitudinal slot 90. Such movement causes drive mechanism 80 to unbend around bend 88, due to the flexibly resilient nature of drive mechanism 80. In particular, initial movement of tab 86 towards the proximal end 32 of housing 30 along longitudinal slot 90 causes bend 88 to move along drive mechanism 80 toward first end 82, until bend 88 is at a position under tab 86, at which it begins to unbend, such that it is bent around an angle of approximately 90°. At this point, bend 88 maintains a stationary position along drive mechanism 80, and begins to further unbend. This in turn causes a biasing force to be exerted between first end 82 and second end 84 of drive mechanism 80. Accordingly, bend 88 moves along drive mechanism 80 toward first end 82, and toward an unbent or straightened position. Since second end 84 of drive mechanism 80 is fixedly attached to tip guard assembly 50, and since tip guard assembly 50 is axially movable along needle cannula 20, such movement and unbending of bend 88 creates a biasing force between drive mechanism 80 and tip guard assembly 50, which causes tip guard assembly 50 to axially move in the opposite direction, i.e., in the direction of arrow 102 away from housing 30 and toward distal end 24 of needle cannula 20, where tip guard assembly 50 can effectively shield puncture tip 28. Lockout leg 74 of tip guard assembly 50 passes distally beyond puncture tip 28 and the inherent resiliency of spring leg 66 urges lockout leg 74 over puncture tip 28, preventing a return movement and thus preventing re-exposure of puncture tip 28.

It is noted that the biasing force exerted between first end 82 and second end 84 of drive mechanism 80 is dependent in part on the length of drive mechanism 80, the initial positioning of bend 88 along drive mechanism 80 within housing 30, the length of longitudinal slot 90, the specific properties of the material forming drive mechanism 80, and the like. Such features can be properly selected and adjusted by the skilled artisan in order to provide the appropriate force required to propel tip guard assembly 50 to the shielding position.

It is noted that activation of the safety feature may be accomplished while venipuncture is maintained, that is while puncture tip 28 of needle cannula 20 is maintained within the blood vessel of the patient. For example, tab 86 can be activated while puncture tip 28 is within the patient's blood vessel, thereby moving tip guard assembly 50 axially along needle cannula 20. Since puncture tip 28 is within the patient's blood vessel, such distal movement of tip guard assembly 50 will terminate when tip guard assembly 50 contacts the skin of the patient near the puncture site. Upon removal of puncture tip 28 from the patient's blood vessel, tip guard assembly 50 will continue in its axial movement toward the distal end 24 of needle cannula 20 due to the bias exerted through bend 88 between first end 82 and second end 84 of drive mechanism 80. Such axial movement results in lockout leg 74 being urged over puncture tip 28 of needle cannula 20, thereby shielding puncture tip 28 of needle cannula 20.

The shieldable needle device of the present invention provides a unique structure for providing safety shielding of a needle tip for protection. The arrangement of the drive mechanism 80 within housing 30 prevents access to the drive mechanism 80, and allows for a simple mechanism for causing actuation of the shielding feature. Moreover, the bent nature of the drive mechanism 80 resulting in the drive mechanism extending in opposing longitudinal directions provides for an added safety feature for activation. In particular, such a bent arrangement allows for the user to activate the shielding feature by moving the operating finger away from the needle tip while simultaneously moving the tip guard assembly 50 forward to the shielding position.

FIGS. 6–10 depict further embodiments of the present invention that include many components which are substantially identical to the components of FIGS. 1–5. Accordingly, similar components performing similar functions will be numbered identically to those components of FIGS. 1–5, except that a suffix "a" will be used to identify those similar components in FIG. 6, a suffix "b" will be used to identify those similar components in FIGS. 7 and 8, and a suffix "c" will be used to identify those similar components in FIGS. 9 and 10.

In the alternate embodiment of FIG. 6, tip guard assembly 50a is provided as a one-piece assembly including a rearward or proximal end 54a and a forward or distal end 56a, with top extent 46a defining the top portion of tip guard assembly 50a for extending longitudinally along a portion of the needle cannula between proximal end 54a and distal end 56a. Top extent 46a bends downwardly at distal end 56a to form front end wall 48a. At proximal end 54a, top extent 46a bends backward to form spring leg 66a which extends back toward the distal end 56a of tip guard assembly 50a, with lockout leg 74a bending upward and backward to form an end wall, as seen in FIG. 6. Proximal end 54a of tip guard assembly 50a includes proximal opening 76a, while distal end 56a of tip guard assembly 50a includes distal opening 78a extending through front end wall 48a. Proximal opening 76a and distal opening 78a are provided for accommodating the needle cannula extending therethrough. The bends in lockout leg 74a enable secure protective engagement with puncture tip 28a of the needle cannula and further enable smooth axial sliding movement of tip guard assembly 50a along the needle cannula.

While the needle assembly of the present invention has been described in terms of an embodiment for use in connection with a blood collection system, it is further contemplated that the needle assembly could be used with other medical procedures, such as in conjunction with a conventional intravenous infusion set, a hypodermic needle assembly, or a double-ended needle assembly for blood collection, all of which are well-known in the art for use with needle devices.

Figure 7:
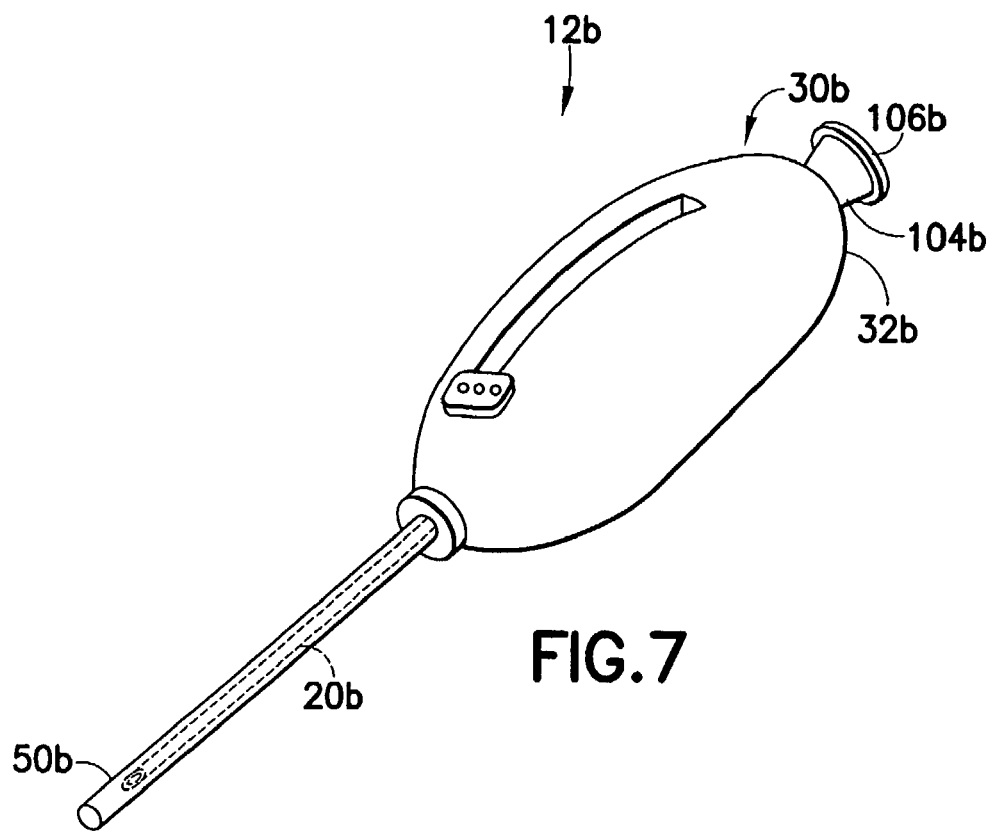
FIG. 7 is a perspective view of a needle device in accordance with a further embodiment of the present invention.
Figure 8:
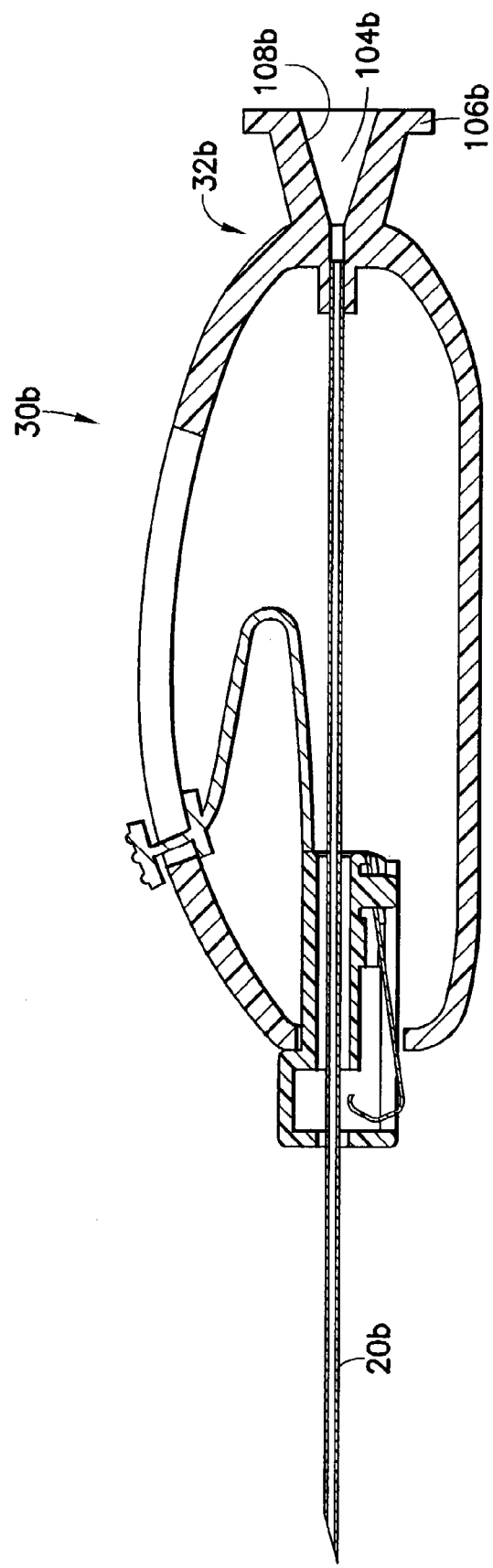
FIG. 8 is a side cross-sectional view of the needle device in FIG. 7.

For example, FIGS. 7 and 8 depict safety needle device 12b for attachment to conventional medical devices, such as conventional needle holders for blood collection, syringes, and the like. As shown in FIGS. 7 and 8, the safety needle device 12b includes a needle cannula 20b, a housing 30b, and a tip guard assembly 50b, as set forth in the embodiment described above. In the embodiment of FIGS. 7 and 8, the safety needle device 12b is an independent component for attachment to a medical device, such as a hypodermic syringe. As such, housing 30b acts as a base housing for providing such attachment.

Accordingly, housing 30b includes means for attachment with a medical device, such as a hypodermic syringe, at proximal end 32b. For example, housing 30b may include a threaded end at the proximal end thereof. Desirably, as shown in FIGS. 7 and 8, housing 30b includes a female luer fitting 104b and a luer flange 106b at the proximal end thereof. Female luer fitting 104b includes an inner tapered surface 108b. Such an arrangement provides for attachment with a luer collar, such as a syringe luer collar. Such a luer fitting enables safety needle device 12b to be sold as a sterile needle device for use with a conventional medical device adapted for use with a luer fitting. Since the safety needle device 12b of FIGS. 7 and 8 is intended for use with a syringe or the like, stabilizers 40 such as those shown in FIGS. 1–3 are not necessarily provided.

Figure 9:
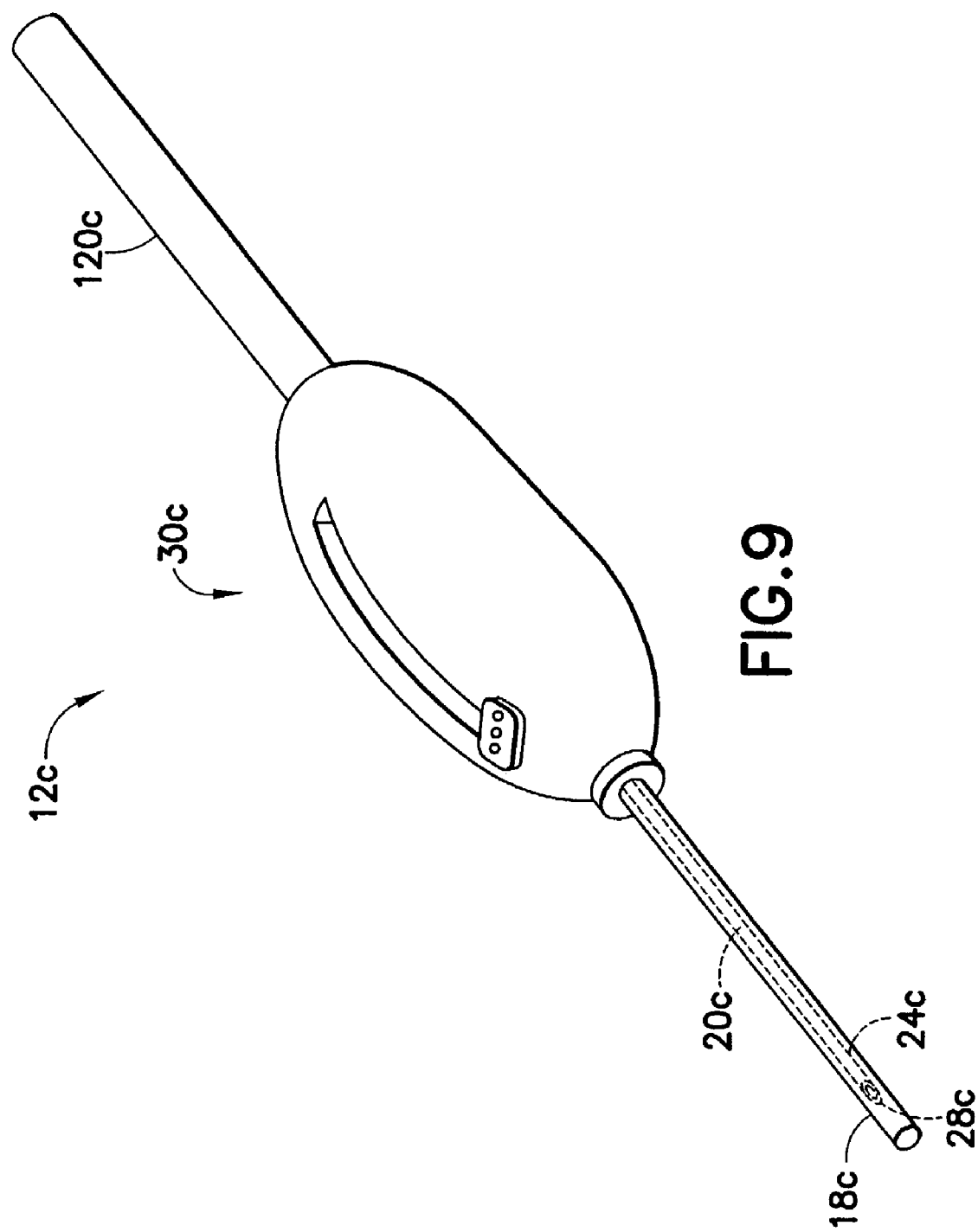
FIG. 9 is a perspective view of a needle device in accordance with yet a further embodiment.
Figure 10:
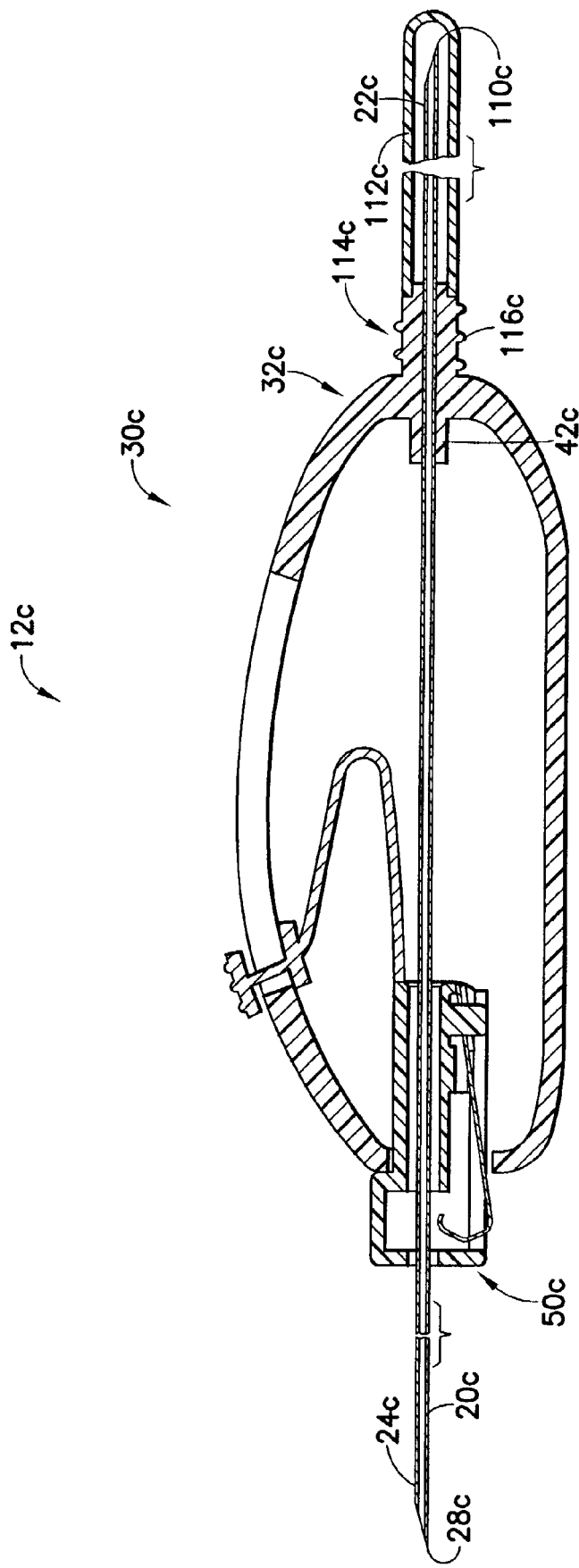
FIG. 10 is a side cross-sectional view of the needle device of FIG. 9.

In a further embodiment depicted in FIGS. 9 and 10, safety needle device 12c is provided as an independent component in the form of a double-ended needle assembly for attachment to a needle holder, as is known for use in connection with blood sampling procedures. In the needle device 12c depicted in FIGS. 9 and 10, needle cannula 20c is in the form of a double-ended needle, including puncture tip 28c as an intravenous puncture tip at distal end 24c thereof, and a non-patient puncture tip 110c at proximal end 22c thereof. Needle cannula 20c extends through hub portion 42c of housing 30c. Proximal end 22c of needle cannula 20c desirably includes an elastomeric sleeve 112c covering non-patient puncture tip 110c.

Housing 30c desirably includes means for attachment to a separate needle holder (not shown). For example, housing 30c may include a threaded end 114c at the proximal end 32c thereof. Preferably, threaded end 114c comprises male threads 116c for mounting needle device 12c on a standard needle holder. As needle device 12c is provided as an independent component for attachment to a separate needle holder, needle device 12c is desirably packaged as shown in FIG. 9, including packaging cover 18c covering distal end 24c of needle cannula 20c, and further including a second packaging cover 120c covering proximal end 22c of needle cannula 20c.

While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A shieldable needle device comprising:
   a housing including a forward end, a rearward end and an internal opening extending therethrough, said housing including a longitudinal slot extending along a wall of said housing between said forward end and said rearward end and through said wall into said internal opening;
   a needle cannula including a forward end and a rearward end, said needle cannula extending from said forward end of said housing;
   a tip guard axially movable along said needle cannula between a retracted position where said forward end of said needle cannula is exposed and an extended position where said tip guard protectively surrounds said forward end of said needle cannula; and
   an elongated flexibly resilient drive mechanism bent within and having at least a portion surrounded by said housing during movement thereof, said drive mechanism including a first end extending through said longitudinal slot at a position adjacent said forward end of said housing and a second end attached to said tip guard,
   wherein movement of said first end of said drive mechanism along said longitudinal slot causes said second end of said drive mechanism to extend, thereby moving said tip guard from said retracted position to said extended position protectively surrounding said forward end of said needle cannula.

2. A shieldable needle device as in claim 1, wherein said drive mechanism is bent around a bend at an angle of about 180° between said first end and said second end.

3. A shieldable needle device as in claim 1, wherein said drive mechanism is a wire.

4. A shieldable needle device as in claim 1, wherein said first end of said drive mechanism includes a tab extending through said longitudinal slot of said housing.

5. A shieldable needle device as in claim 4, wherein said tab includes a surface having a profile for accommodating a user's finger.

6. A shieldable needle device as in claim 1, wherein movement of said first end of said drive mechanism along said longitudinal slot in a direction toward said rearward end of said housing causes said drive mechanism to extend from a bent position to an extended position, thereby moving said tip guard.

7. A shieldable needle device as in claim 1, wherein said housing includes a pair of generally planar wings extending from opposing sides of said housing.

8. A shieldable needle device as in claim 1, wherein said housing is adapted for connection to a blood collection receptacle.

9. A shieldable needle device as in claim 1, wherein said housing further includes means for attachment with a hypodermic syringe.

10. A shieldable needle device as in claim 1, including a packaging cover extending over said needle cannula.

11. A shieldable blood collection set comprising:
a flexible tube having opposed first and second ends, said first end of said flexible tube being adapted for connection to a blood collection receptacle;
a housing mounted to said second end of said flexible tube, said housing including an elongated tubular body having a proximal end, a distal end and an internal passageway extending therethrough, said housing further including a slot extending longitudinally along a wall of said tubular body into said internal passageway;
a needle cannula extending from said distal end of said housing, said needle cannula including a proximal end and a distal end having a puncture tip;
a tip guard adjacent said distal end of said housing and axially movable along said needle cannula between a retracted position where said puncture tip of said needle cannula is exposed and an extended position where said tip guard covers said puncture tip of said needle cannula; and
an elongated flexibly resilient drive mechanism extending within said housing from a first end which extends through said slot at a position adjacent said distal end of said housing, toward said proximal end of said housing, around a bend at an angle of about 180° within said housing, and toward said distal end of said housing to a second end of said drive mechanism which is anchored to said tip guard, at least a portion of said resilient drive mechanism being surrounded by said housing during movement thereof;
wherein movement of said first end of said drive mechanism along said slot in a direction toward said proximal end of said housing causes said second end of said drive mechanism to extend through said distal end of said housing, thereby moving said tip guard from said retracted position to said extended position covering said puncture tip of said needle cannula.

12. A shieldable blood collection set as in claim 11, wherein said drive mechanism is a wire.

13. A shieldable blood collection set as in claim 11, wherein said first end of said drive mechanism includes structure for accommodating a user's finger extending through said longitudinal slot of said housing.

14. A shieldable blood collection set as in claim 11, wherein said housing includes a pair of generally planar wings extending from opposing sides of said tubular body.

15. A shieldable blood collection set as in claim 11, including a packaging cover extending over said needle cannula.

16. A shieldable needle device, comprising:
a housing including a forward end and a rearward end, a needle cannula extending from said forward end of said housing including a puncture tip at a forward end thereof for insertion into a skin surface of a patient;
a shielding assembly axially movable along said needle cannula for shielding said puncture tip of said needle cannula; and
an activation mechanism for causing axial movement of said shielding assembly along said needle cannula,
wherein movement of said activation mechanism away from the patient causes said shielding assembly to move axially toward the skin surface; and
wherein said activation mechanism comprises an elongated flexibly resilient wire extending within said housing, said wire being bent around a bend at an angle of about 180° within said housing between a first end and a second end of said wire such that at least a portion of said second end of said wire is surrounded by said housing during movement therein.

17. A shieldable needle device as in claim 16, wherein said housing includes a longitudinal slot extending therethrough, and said wire includes a first end which extends through said slot at a position adjacent the forward end of the housing and a second end which is anchored to said shielding assembly.

18. A shieldable needle device, comprising:
a housing including a forward end and a rearward end,
a needle cannula extending from said forward end of said housing and fixed with respect to the housing, the needle cannula including a puncture tip at a forward end thereof for insertion into a skin surface of a patient;
a shielding assembly axially movable along said needle cannula for shielding said puncture tip of said needle cannula; and
an activation mechanism entirely movable with respect to the housing and having a first portion extending externally to the housing and a second portion in engagement with the shielding assembly such that movement of the first portion of said activation mechanism with respect to the housing in a direction continuously away from the puncture tip and adjacent the rearward end of the housing causes corresponding movement of the entire activation mechanism, thereby simultaneously moving the portion of the activation mechanism is engagement with the shielding assembly forward toward the puncture tip to cause said shielding assembly to move axially toward the puncture tip.

19. A shieldable needle device as in claim 18, wherein said shielding assembly comprises a tip guard.

20. A shieldable needle device as in claim 18, further comprising a packaging cover extending about said needle cannula.

21. A shieldable needle device as in claim 18, wherein at least a portion of said second portion of said second activation mechanism is surrounded by said housing during movement of said activation mechanism.

* * * * *